(12) United States Patent
Quadling et al.

(10) Patent No.: US 7,670,272 B2
(45) Date of Patent: Mar. 2, 2010

(54) MILLING MACHINE WITH TOOL CHANGER POSITIONABLE WITHIN MOTION SYSTEM ENVELOPE

(75) Inventors: Mark S. Quadling, Plano, TX (US); Henley S. Quadling, Dallas, TX (US); Rod Duncan, Plano, TX (US)

(73) Assignee: D4D Technologies, LLC, Richardson, TX (US)

( * ) Notice: Subject to any disclaimer, the term of this patent is extended or adjusted under 35 U.S.C. 154(b) by 0 days.

(21) Appl. No.: 12/360,637

(22) Filed: Jan. 27, 2009

(65) Prior Publication Data
US 2009/0148252 A1 Jun. 11, 2009

Related U.S. Application Data

(60) Division of application No. 11/756,650, filed on Jun. 1, 2007, now Pat. No. 7,497,817, which is a continuation-in-part of application No. 11/062,986, filed on Feb. 22, 2005, now Pat. No. 7,270,592, which is a continuation-in-part of application No. 10/917,069, filed on Aug. 12, 2004, now Pat. No. 7,226,338.

(51) Int. Cl.
*B23Q 3/157* (2006.01)

(52) U.S. Cl. .................... 483/1; 483/10; 483/2; 483/57

(58) Field of Classification Search .............. 483/1, 483/30–33, 54–57, 51, 59, 60, 61, 66, 10–11, 483/9, 12, 2
See application file for complete search history.

(56) References Cited

U.S. PATENT DOCUMENTS

| 4,411,626 | A | | 10/1983 | Becker et al. |
|---|---|---|---|---|
| 4,499,650 | A | | 2/1985 | Cannon et al. |
| 4,520,551 | A | | 6/1985 | Imhof |
| 4,641,413 | A | | 2/1987 | Hallqvist et al. |
| 4,700,452 | A | * | 10/1987 | Babel .......................... 483/54 |
| 4,706,371 | A | | 11/1987 | McMurtry et al. |
| 4,730,373 | A | | 3/1988 | Senoh |
| 5,111,573 | A | | 5/1992 | Ito et al. |
| 5,230,685 | A | | 7/1993 | Christen et al. |
| 5,803,886 | A | | 9/1998 | Schweizer et al. |
| 6,394,880 | B1 | | 5/2002 | Basler et al. |

(Continued)

FOREIGN PATENT DOCUMENTS

DE 10235873 A1 2/2004

(Continued)

*Primary Examiner*—Erica E Cadugan
(74) *Attorney, Agent, or Firm*—Haynes and Boone LLP

(57) ABSTRACT

An improved milling machine makes use of individually controlled x-axis, y-axis, and z-axis carriages. These carriages provide positive and precise control of the position of the cutting tools and the blank to be cut. The tools are located in spindles that are moved in the x-axis. A work piece or blank is manipulated in the y-axis and the z-axis. The tools are offset in the x-axis. Lights on a work space door are used to signal the condition of the mill machine and the milling operation. A tool changer allows the tools to be changed to accommodate other materials. A camera or other sensor is used to detect the location and wear on the tools.

20 Claims, 12 Drawing Sheets

U.S. PATENT DOCUMENTS

| | | |
|---|---|---|
| 7,226,338 B2 | 6/2007 | Duncan et al. |
| 7,270,592 B2 | 9/2007 | Duncan et al. |
| 7,497,817 B2 * | 3/2009 | Quadling et al. .............. 483/56 |
| 2006/0269373 A1 | 11/2006 | Duncan et al. |
| 2007/0111640 A1 | 5/2007 | Bem et al. |
| 2007/0197361 A1 | 8/2007 | Boehler et al. |

FOREIGN PATENT DOCUMENTS

| | | |
|---|---|---|
| WO | 2006005545 A1 | 1/2006 |

* cited by examiner

MILLING MACHINE WITH TOOL CHANGER POSITIONABLE WITHIN MOTION SYSTEM ENVELOPE

CROSS REFERENCE TO RELATED APPLICATION

The present disclosure is a division of and claims priority to U.S. application Ser. No. 11/756,650, filed Jun. 1, 2007, now U.S. Pat. No. 7,497,817, which is a continuation-in-part of U.S. application Ser. No. 11/062,986, now U.S. Pat. No. 7,270,592, filed Feb. 22, 2005, which is a continuation-in-part of U.S. application Ser. No. 10/917,069, now U.S. Pat. No. 7,226,338, filed Aug. 12, 2004, each of which is hereby incorporated by reference in its entirety.

TECHNICAL FIELD OF THE INVENTION

The present invention relates to an improved milling machine that is used to mill a crown or dental implant from a blank. The milling machine is adapted to receive instructions from a separate scanner that provides a memory in the milling machine with data on the outer and inner contours for the milled crown. The improvements include the use of coaxially offset spindles and a means for visually informing a user of the status of a particular mill job.

BACKGROUND TO THE INVENTION

One of the most common procedures for a dentist is the repair of a broken tooth. When a tooth is broken, a portion of the enamel comes off, exposing the dentin underneath. The dentin must be covered to prevent the dentin from becoming infected. The dentist will grind a portion of the remaining enamel away to prepare the tooth for a crown. Once the grinding procedure is complete, a reduced stump remains and a mold of the stump is made with a quick setting mold material. Further a mold of the adjacent teeth and the opposing teeth are also made. Then a temporary crown in placed on the stump. The temporary crown has been partially customized to fit over the stump and to mesh with the opposing teeth. However, due to traditional time constraints, the temporary crown rarely feels as natural as the original tooth. Further, the temporary crown must be affixed to the stump with a temporary fixative.

With the mold as a guide, an outside laboratory will prepare a permanent crown. The permanent crown may be made of porcelain, gold, ceramic, or other metal or substance. This process usually takes at least three weeks to complete. During this time, the patient must function with the temporary crown. Unfortunately, there is a risk that the temporary crown may loosen and be swallowed or otherwise lost by the patient. Even if it only loosens, bacteria can gain access to the dentin for a time and cause more serious dental health issues. Also, once the permanent crown is available for placement, the temporary crown must be removed. This requires the dentist to twist the temporary crown off the stump, exerting a significant torque to the roots. Even then, if the permanent crown is misshaped, then it may need to be removed again and remade.

A need exists for a method of improving the speed of producing a permanent crown for a patient. Indeed, if the crown could be produced while the patient waited, it would be a great savings for the patient and the dentist both. Moreover, it would also be beneficial to eliminate the need to make a temporary crown at all.

Sirona Dental Services GmbH, of Bensheim Germany produces a milling machine specifically for producing porcelain crowns. It is disclosed in U.S. Pat. No. 6,394,880 discloses one aspect of this milling machine. It allows for the use of two milling bits to simultaneously work a blank to form it into a permanent crown. The mill bits are located on opposite sides of the blank and can move in an x-, y-, and z-plane. However, the bits can not be changed on demand to accommodate a different blank material. Also, there is no method disclosed for determining the bit wear to warn the dentist that the crown's dimensions may be skewed due to bit wear.

The Sirona patent illustrates a portion of a larger milling machine known as the CEREC. The CEREC has several other drawbacks. First, it has only a wireless connection with an intraoral digitizer used to make the measurements of the stump and adjacent teeth. Once the measurements are made, the intraoral digitizer cannot be used until the crown is finished. Therefore, a need exists for a milling machine that includes a memory that can store the required data thereby freeing the intraoral digitizer to be used again. Further, the CEREC device is flawed in its failure to minimize vibration that affects the quality of the milling. Even minor vibration can create many microns of error on the surface of the crown.

SUMMARY OF THE INVENTION

The present invention overcomes many of the defects of the prior art and allows the dentist to mill a superior permanent crown or other dental inlay while the patient waits. This reduces the amount of time for the patient in the dentist chair, thereby allowing the dentist to schedule more patients. Further, it is a significant time savings for the patient. The milling machine can be located at the dentist office. However, it could also be located at a traditional dental lab. In this event, the lab would receive the data outlining the contours for the crown or the inlay. It would still be able to supply a superior crown or inlay in less time than traditionally experienced.

The present milling machine is characterized by a robust and sturdy frame that minimizes any vibration. This helps ensure the highest quality end product. Further, the spindles that rotate the milling bits are located on a common rail, giving the device the ability to move the tools in the x-axis. The blank is releasably attached to a mandrel. The mandrel is secured to a subassembly that allows motion in the y-axis and the z-axis. It must be understood that the tools could be manipulated in the y-axis or z-axis while the blank is manipulated in the other axes. The milling machine includes a CPU and memory for storing the data on the contour of the crown or inlay. Further, the milling machine has a water reservoir for settling any particulate that becomes entrained in the water used to cool and rinse the blank during milling.

Tools used to mill the blank can be changed using a novel automatic tool changer. The ability to engage different tools also allows for the use of different blank materials, from hardened metals to ceramics to porcelain to gold. Further, a camera or other sensing device can be used to monitor wear experienced by the tools. The blank is held by a mandrel that engages a frame within a work area that is easily accessible to a technician or the dentist. While this disclosure focuses on the production of crowns, it should be understood that this term is being used broadly. Indeed, while a crown is one of the preferred items for milling, this improved milling device could be used to produce dental items such as inlays, onlays, coping, framework, bridges, implants, implant abutments, veneers, and overlays, and the like.

The present invention is also unique in that it utilizes a pair of spindles that are not co-axially aligned in the x-axis. Indeed, there is an offset that is roughly equal to or greater than the diameter of one of the tools used. Another unique aspect involves the use of lights to illuminate the work chamber. One color can indicate that a job is in progress, while another color might indicate that a job is complete. This provides the technician with feedback that is understood at a glance. Yet another aspect of the present invention is the use of left handed mill tools. By having the tool threaded in a direction opposite the direction of rotation, the tool is less likely to advance out of the spindle. Minimizing the risk of an advancing tool also minimizes the risk of error in producing the milled surfaces.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE DRAWINGS

This inventive milling machine is sized to fit on the countertop of a dentist office or in a lab. Its generally compact size however does not mean that the quality of end product is diminished. Instead, the milling machine is built so robustly that it will produce the highest quality crowns and inlays. An intra-oral digitizer is used to measure the dimensions of the prepared tooth, as well as the adjacent and opposed teeth. Software within the digitizer constructs an outer contour that meshes with the adjacent and opposing teeth. The design is approved by the dentist and then conveyed to the milling machine.

Figure 1:
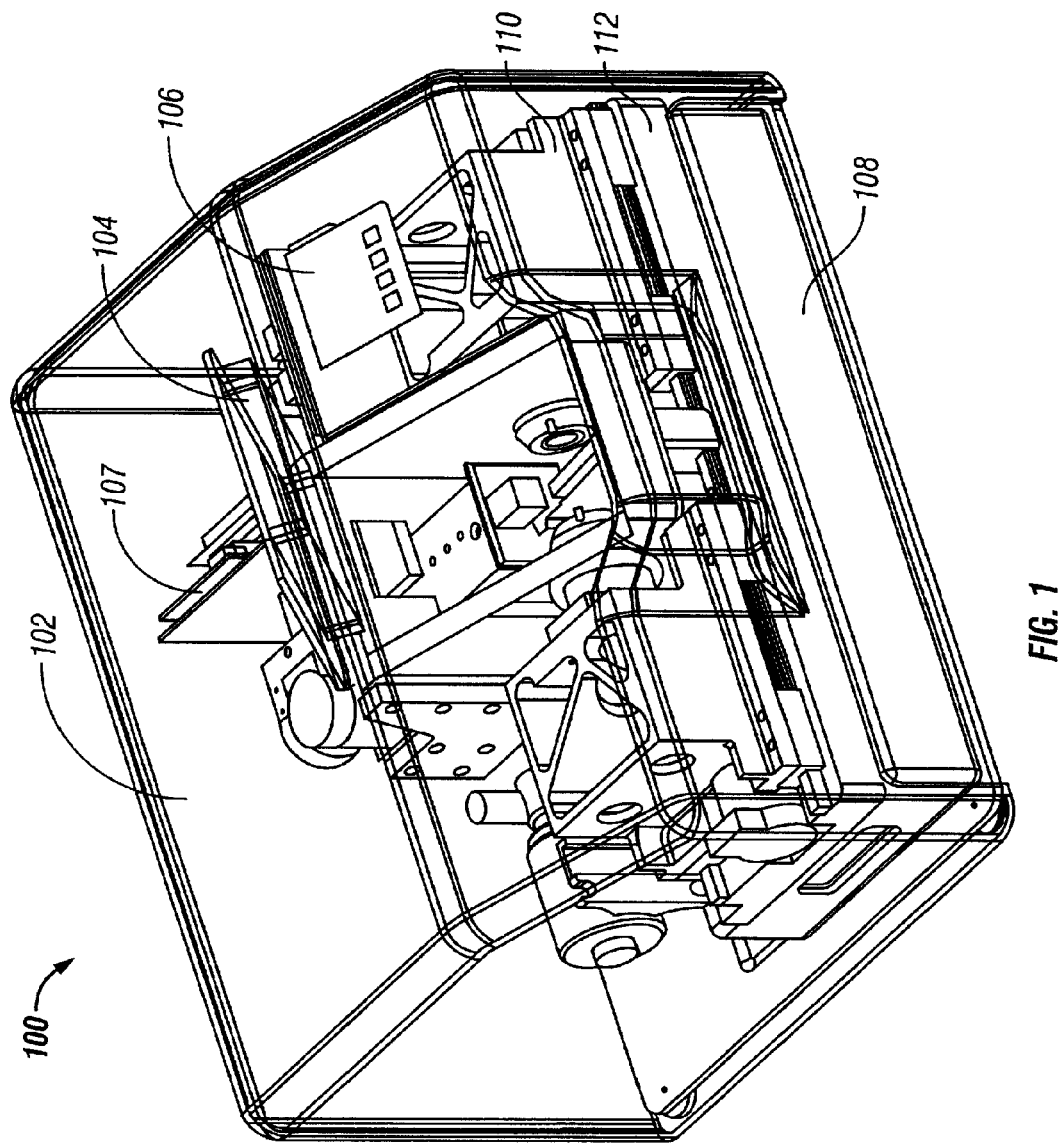
FIG. 1 is a perspective view of a milling machine that embodies the present invention.
Figure 2:
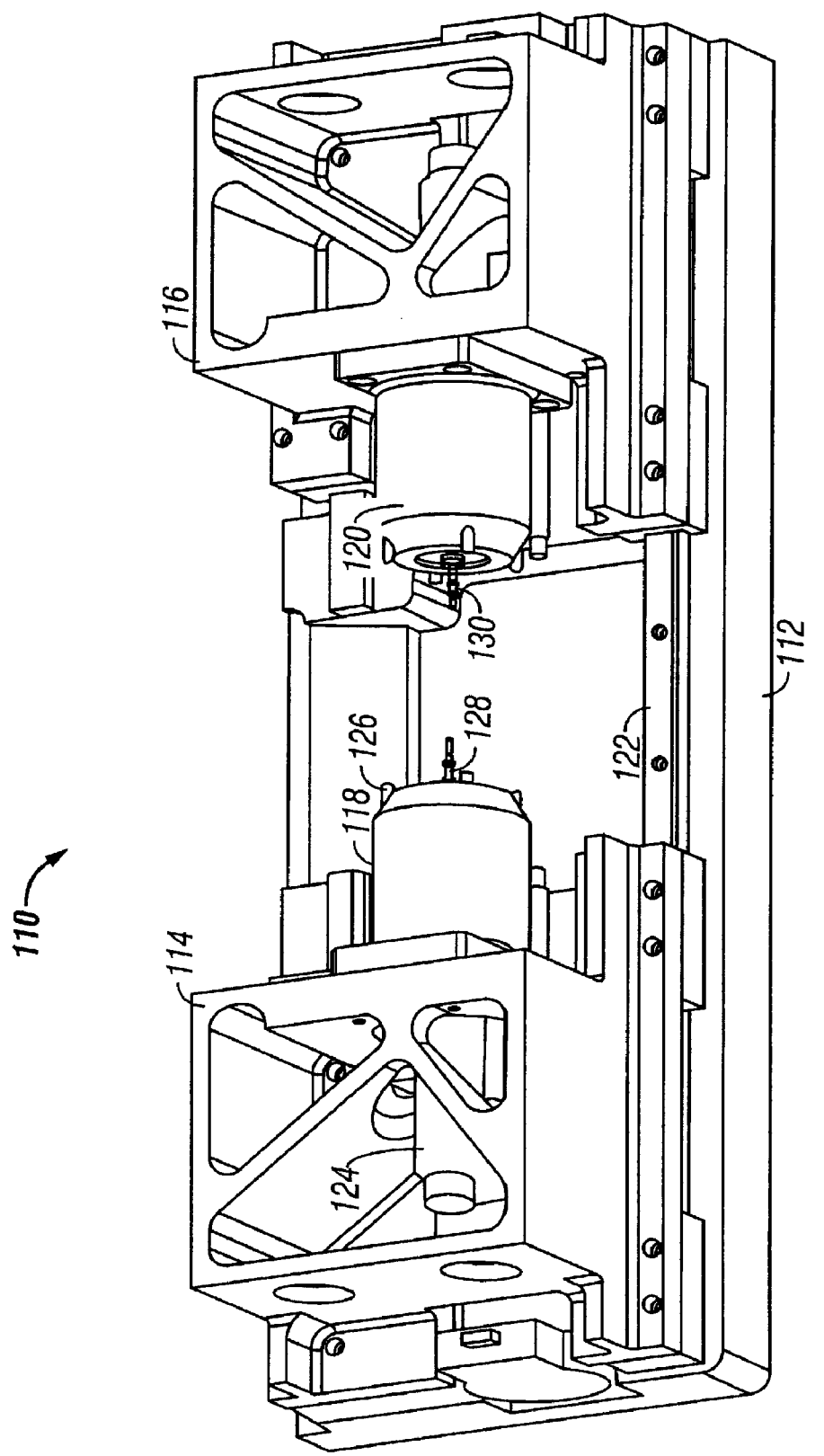
FIG. 2 is perspective showing the carriage that controls the x-axis movement of the spindles.

FIGS. 1 and 2 provide perspective views of the milling machine 100. It includes a cover 102 that protects the operator from the moving parts within. A blank 10 is held within a work area that is accessible through door 104. The x-axis carriage 110 is used to move the tools back and forth into engagement with the blank 10. The carriage 110 includes a first and second frame that both slide on rails on subframe 112. The subassembly 140 is used to control the y-axis and z-axis movement of the mandrel and blank. While the tools are manipulated in the x-axis, this is just an issue of reference. The tools could be manipulated in the y-axis and the blank moved in the x-axis and z-axis. Alternatively, the tools could be manipulated in the z-axis and the blank manipulated in the x-axis and y-axis. A reservoir is also located at the bottom of the machine 100. The CPU, memory and other electronics are located in compartment 107. These can be controlled, or activity displayed on display 106.

FIG. 2 is an isolated view of the x-axis carriage 110. It includes a first frame 114 and a second frame 116. In one embodiment, these frames are formed from a single block of metal, having no seems to decrease their stiffness. A first and second spindle 118, 120 are coupled to these frames 114, 116. The frames 114, 116 move on a single pair of rails 122 to ensure absolute alignment. Each frame is coupled to a first and second spindle, wherein each spindle has a central axis. In this embodiment, the central axis of each spindle is aligned. However, as discussed below in reference to FIG. 9 the axis of each spindle can also be offset. Tools 128 and 130 are accepted into the spindles along this axis. The spindles rotate the tools so that a cutting surface on the tool can carve away material from the blank as desired. Of course, this process generates heat and carvings. A fluid stream emits from the spindle ports 126 as well to wash and cool the blank during milling. This effluent exits to a reservoir where particulate matter can settle. Motors 124 are used to supply the power to move the frames along the rails and to rotate the tools within the spindles.

Figure 3:
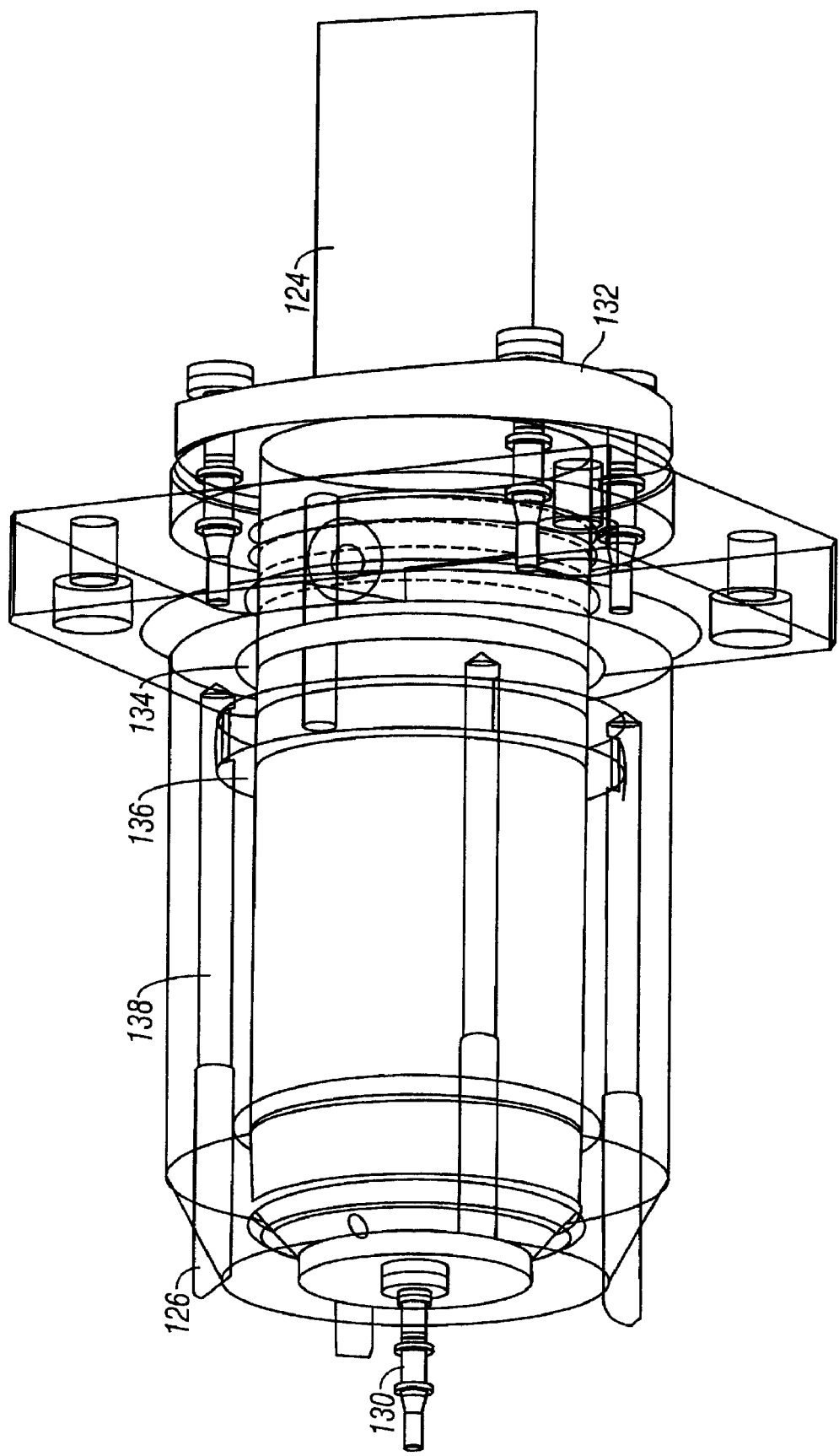
FIG. 3 is a cut-away view of the spindle showing the collet that engages the cutting tool and the cooling fluid delivery path.

FIG. 3 provides a more detailed view of the spindle 120 and the tool 130. Water, or other cooling fluid, is fed into the spindle through supply 124. Water passes through passages 132 into a collar 136. This collar supplies the water into several tubes 138 that carry the water to the front of the spindle. The water is sprayed from the tips of the tubes 138 and directed toward the tip of the tool 130. At least one o-ring is used to seal and separate the spindle's motor from the water.

Figure 4:
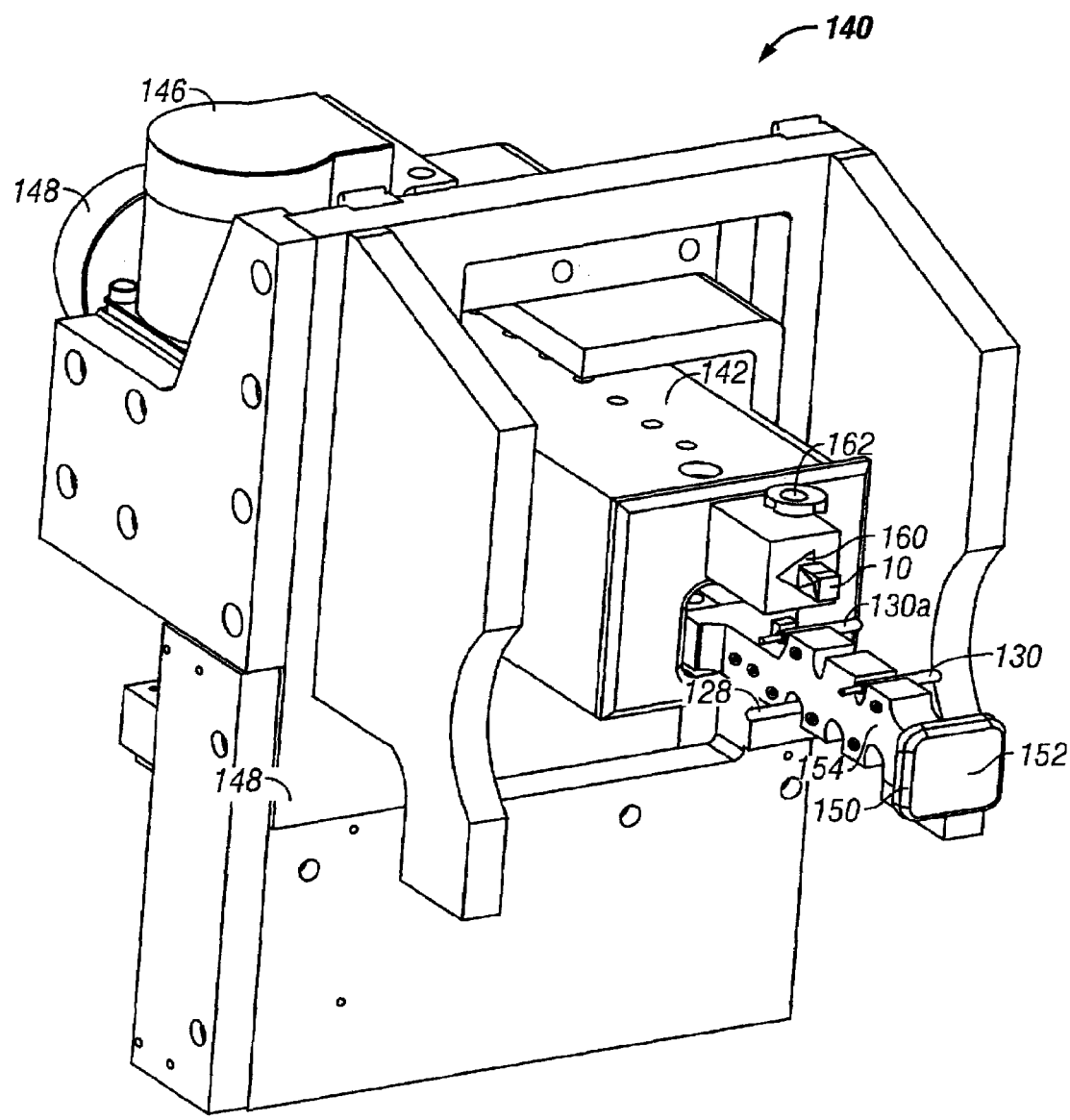
FIG. 4 is a perspective view of the subassembly that controls the y-axis and z-axis of the device.

The complex outer contour of the damaged tooth is reproduced by the present milling machine. This requires an accurate understanding of exactly the location of the tip of the tools and the x, y, z coordinates of the blank. Thus the shape and length of the mandrel 160 holding the blank must be precise. Very precise motors are used to move the carriages shown in FIG. 3. This same level of precision is reproduced for the y and z axes. However, rather than move the spindles, the mandrel is moved in the y and z axes by the subassembly 140 shown in FIG. 4. In FIG. 4, the y-axis is controlled by moving a carriage along rails. A separate z-axis carriage 142 includes the frame for engaging the mandrel 160 and automatic tool changer 130. This view also illustrates the location of the mandrel 160 and blank 10 to be milled. It is located on the z-axis carriage. A cam 162 is used to secure the mandrel in place. The mandrel and blank will be shown in greater detail below. The automatic tool changer 150 is also attached to the z-axis carriage. The tool changer can carry several additional tools 128, 130 for placement into the spindles. The tool changer 150 also includes at least one open port 154 for accepting the tool in the spindle. An electronics package 152 can be located on the end of the tool changer 150.

Figure 5:
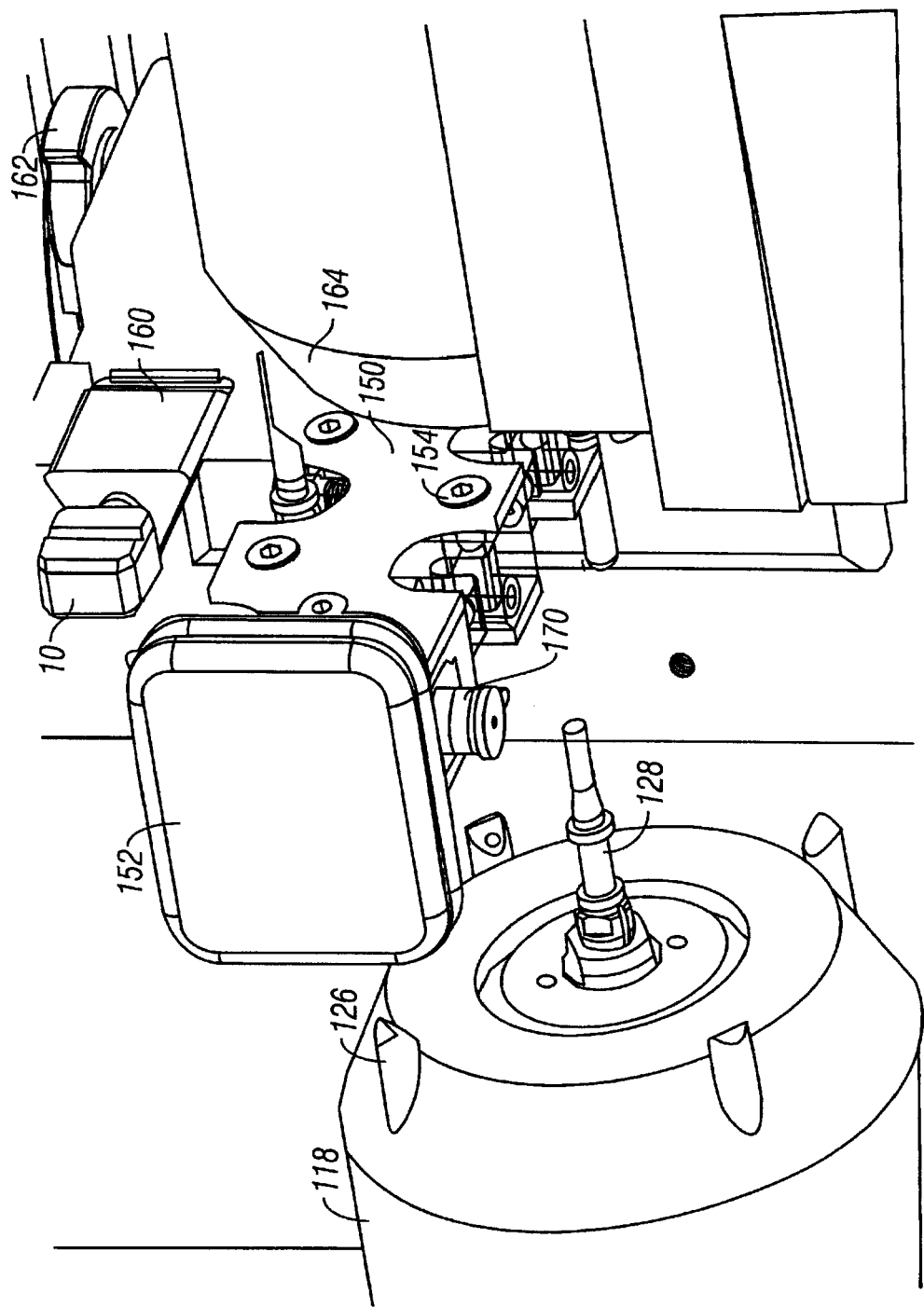
FIG. 5 is an enlarged view showing the automatic tool changing machine and the digital camera used to detect tool wear and axial calibration.

FIG. 5 provides an even more detailed view of the tool changer 150, blank 10, and tools. In this view, the y-axis carriage has moved the blank 10 above the tool 128. In this position, a camera 170 can be used to inspect the condition of the tip of tool 128. Note that the tool 128 is co-axially located within the spindle 118. Further, note that the nozzles 126 are angled to direct a cooling spray of fluid onto the tip of the tool 128. In another embodiment, a camera is not used. Instead the tool is positioned in a slot on the tool changer where its position is detected, and its shape and size is calculated. As the tool is moved into the slot and past a sensor, the upper edge is detected. The entire tool is advanced past the sensor. The tool is then lowered and its lower edge is detected. This allows the calculation of the tool's diameter. The tool is moved so that its midline is even with the sensor. The tool is then backed out until the tip of the tool is detected. This method allows the general measurements of the tool to be determined.

Figure 6:
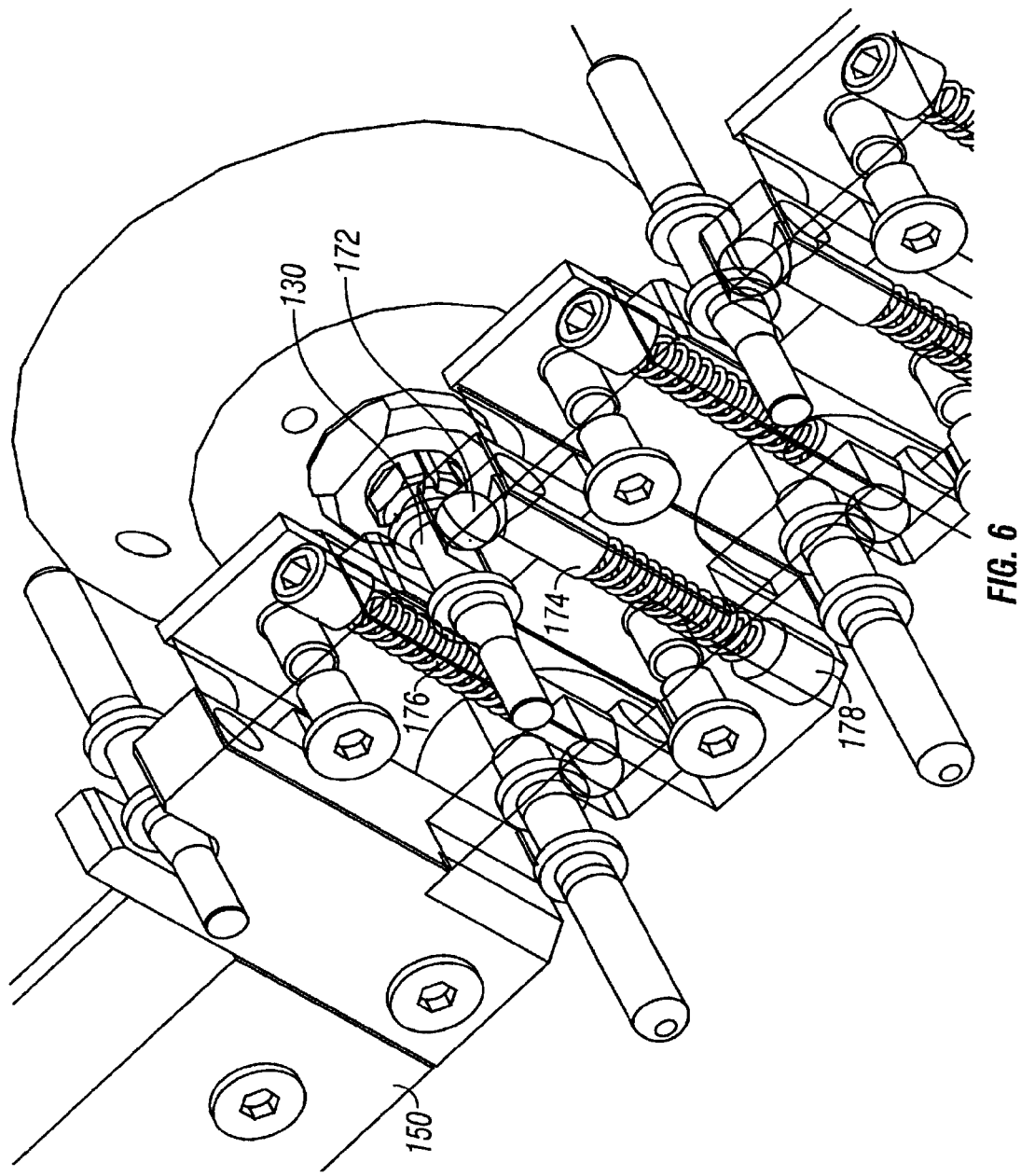
FIG. 6 is an enlarged perspective showing the engagement between the tool in a spindle and the automatic tool changer.

One of the important advances of the present invention is the ability to substitute tools as required. For example, a tool for grinding a contour onto a ceramic is different than a tool for grinding a contour onto a blank of gold. The prior art has never addressed the need for a lab to be able to quickly deal with blanks of differing materials. The present invention can allow a technician to simply enter the desired material. The user interface display 106 on the milling machine may instruct the user as to which material to use, or the type of material may be automatically detected by the milling machine, by means of a barcode scan or RFID identification or the like. The milling machine will engage the appropriate tool for the material. The camera 170 will inspect the tool for wear and if necessary, select a backup tool for the process. Alternatively, if the tool is too worn and no back-up is available, the technician will be alerted. The ability to engage and disengage the tools is shown in FIG. 6. The tool changer 150 is positioned with the y-axis carriage to a position in between the spindles. The selected tool is positioned in co-axial relationship with the spindle using the z-axis carriage. A collet on the spindle is opened to engage the distal end of the tool, for example tool 130. The tool is releasably secured in the tool changer 150 with a spring loaded ball 172 or other means for securing the tool. Ball 172 presses against a central portion of the tool between a first and second flange. When the tool is engaged in the spindle, its collet closes. The tool changer 150 is then lowered with the y-axis carriage. This forces the ball 172 against pin 174 and compressed spring 176. The force on spring 176 can be adjusted using the set screw 178.

Figure 7:
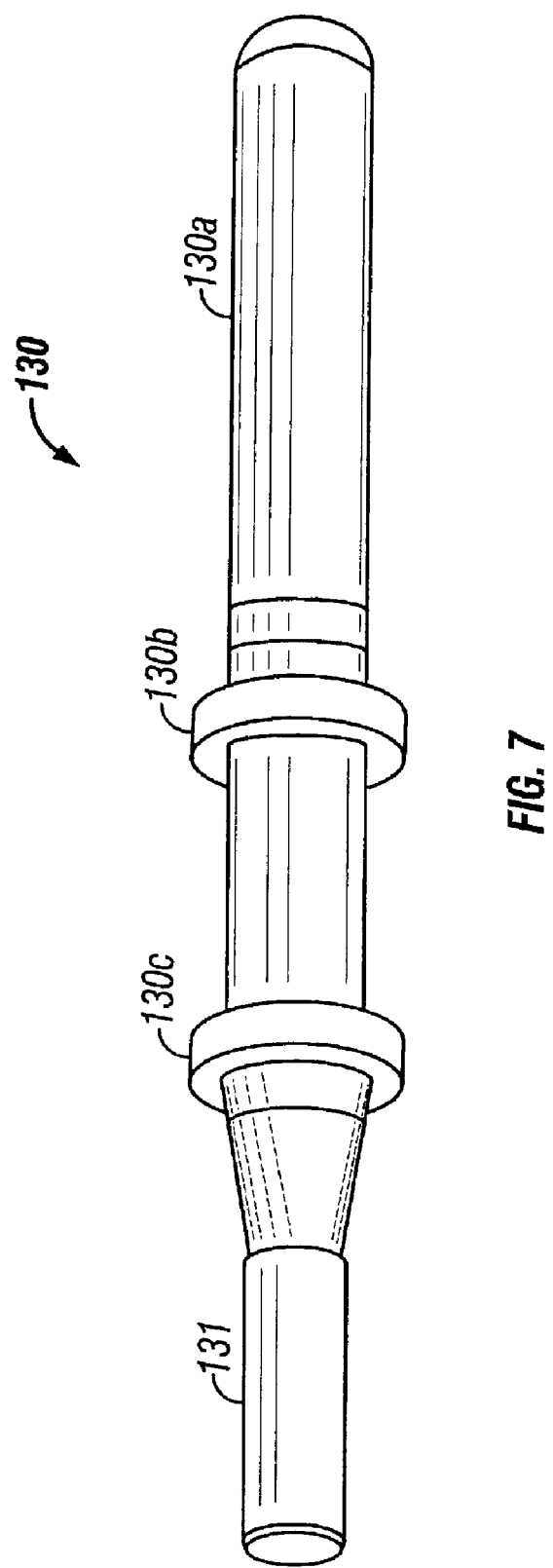
FIG. 7 is a perspective view of a tool that can be used in the present embodiment.

FIG. 7 provides a more detailed illustration of the tool 130. It includes a distal end 130a that is engaged within the spindle. At least 25% of the length of the tool is engaged within the spindle to ensure stability and to minimize and bending of the tool. The proximal end 131 of the tool can vary based on the material to be milled. For example, the grinding tip shown is for a ceramic. However, another tip might be used for grinding away a metal blank. Flanges 130b and 130c define a central portion that is used to engage the tool to the tool changer 150. However, the flanges serve the additional purpose of assisting with the registration of the tool and the blank. In other words, even though the exact length of the tool is known, the x, y, z coordinates of its tip must still be known exactly. When the tool is engaged into the spindle, the flange acts as a travel limit and thus defines the distance between the tip and the spindle. Thus, when the spindle moves along the x-axis, the position of the tip of the tool will be known.

Figure 8:
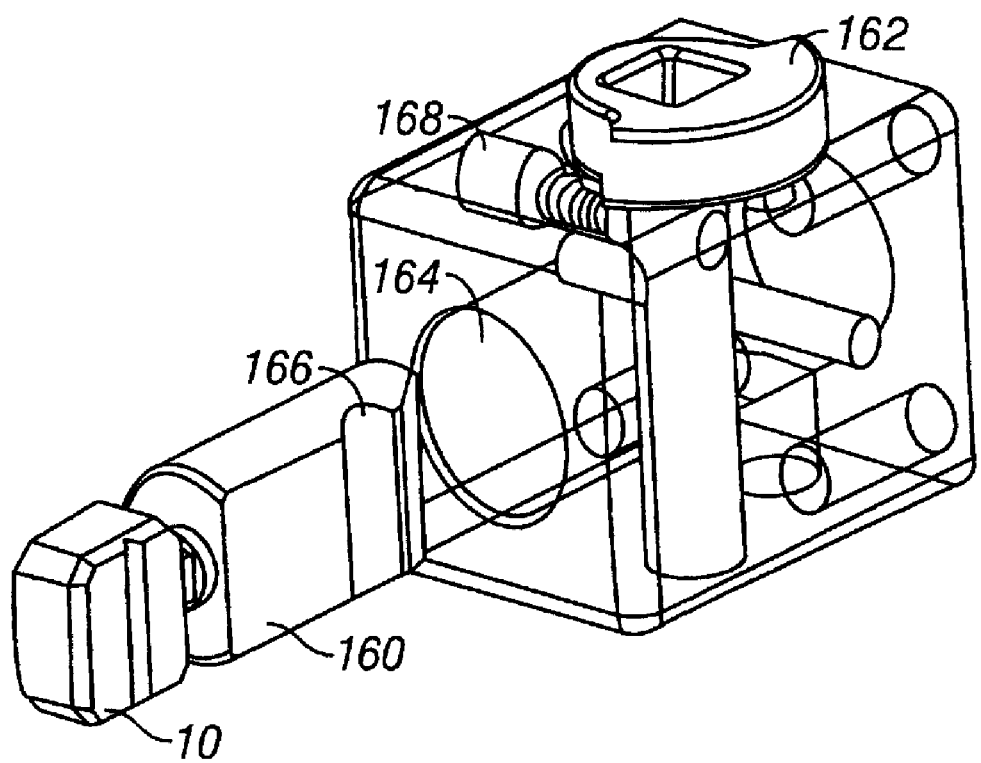
FIG. 8 is an exploded view of the mandrel and blank.

In addition to knowing the exact x, y, and z coordinates of the tool tips, it is also essential to know the exact position for the blank. This requires that the mandrel and blank be consistently placed into the machine. The mandrel and blank engage a mandrel socket 164 that in turn engages the z-axis carriage. FIG. 8 shows the mandrel socket in more detail. The mandrel 160 has a distal end that enters a similarly shaped socket 164. As shown the mandrel has a generally circular cross-section that engages the generally cylindrical socket. A groove 166 near the distal end of the socket provides an engagement surface for a cam 162. The cam 162 is rotated to a first position to allow insertion of the mandrel 160. The cam 162 is then rotated to a second position that engages the groove and secures the mandrel within the socket. A pin 168 is used to prevent the accidental rotation of the cam. While a cylindrical mandrel is shown, its cross-section could be any suitable shape. Note that the socket has an opening on both ends. This allows for debris to be pushed through the socket rather than allow it to build up within the socket. After placement in the milling machine, there may be some other detection means to refine the knowledge of the precise location of the blank with respect to the other parts of the milling machine. The additional detection means may comprise optical or touch probe means.

Figure 9:
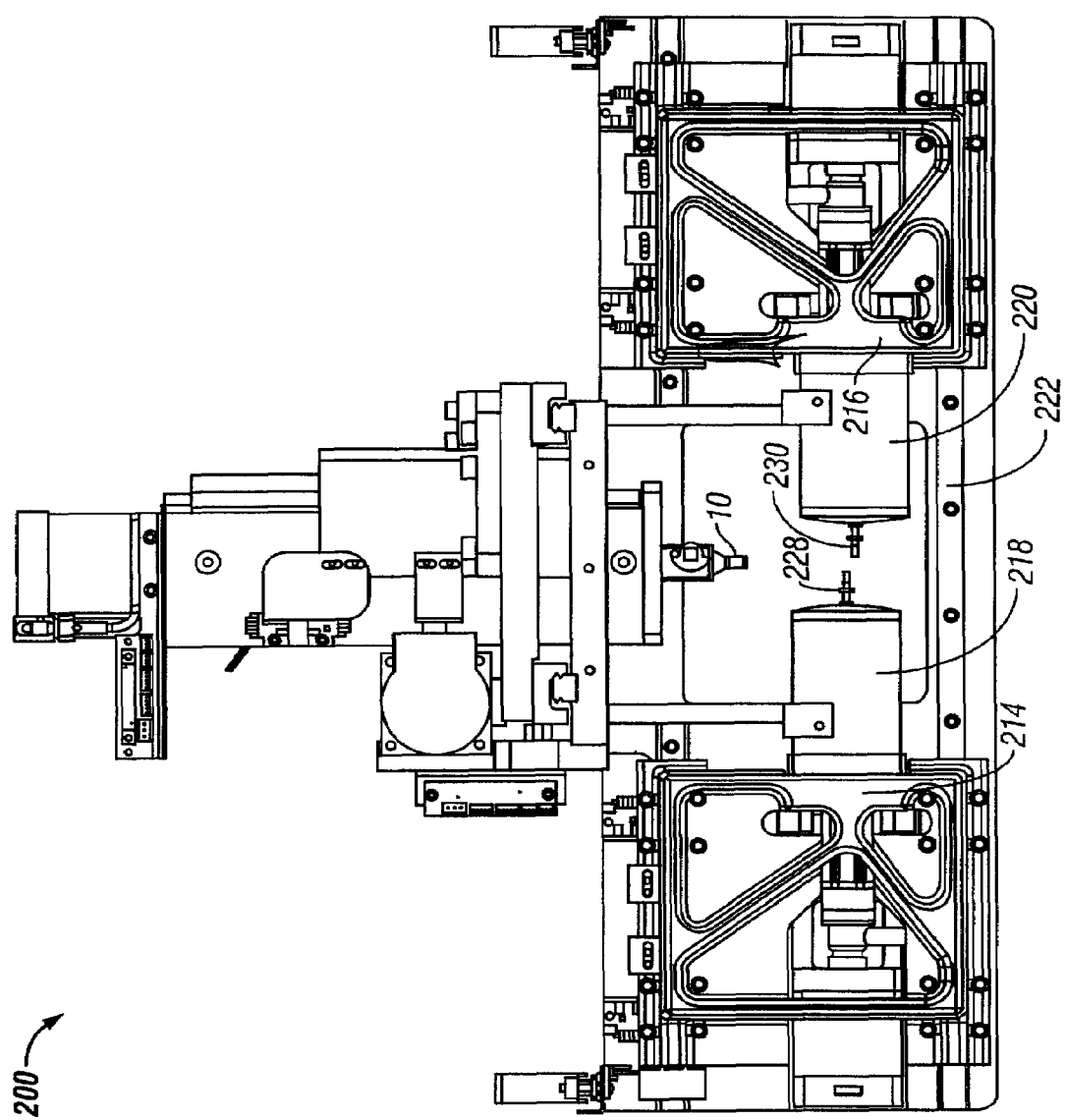
FIG. 9 is a top view of the carriage that controls the x-axis movement for an alternate embodiment.

FIG. 9 is a top view of the x-axis carriage for an alternate embodiment of the milling machine 200. It includes a first frame 214 and a second frame 216. In one embodiment, these frames are formed from a single block of metal, having no seems to decrease their stiffness. A first and second spindle 218, 220 are coupled to these frames 214, 216. The frames 214, 216 move on a single pair of rails 222. Each frame is coupled to a first and second spindle, wherein each spindle has a central axis. In this embodiment, the central axis of each spindle are offset rather than aligned. In one embodiment, the offset can be roughly equal to or slightly greater than the diameter of a tool. Tools 228 and 230 are accepted into the spindles. The spindles rotate the tools so that a cutting surface on the tool can carve away material from the blank as desired. Of course, this process generates heat and carvings. A fluid stream emits from the spindle ports (not shown) as well to wash and cool the blank during milling. This effluent exits to a reservoir where particulate matter can settle. While the offset is shown in x-axis, it could also be in the y-axis.

There are several advantages to having the tools offset in the x-axis. It decreases the chance of the tools tapping each other after completion of the milling process. It also decreases the chances of "pinching". While the tools move over the blank 10, it begins to take the shape of a crown or other dental implant. A neck portion or "sprue" connects the milled shape to the mandrel. In other words, the milled blank is not severed from the mandrel. This neck portion has a greatly reduced diameter and can be easily trimmed by the technician to remove the crown from the mandrel. By leaving the crown attached to the mandrel reduces the risk of the crown being damaged when it falls within the work chamber. However, milling the sprue requires that the tools work on opposite sides of an ever decreasing amount of blank material. The tools are being rotated in opposite directions at very high speeds, on the order of 35,000-40,000 rpm. As the amount of material between them decreases, the tips of the tools can cause the neck to deflect and pinch the opposing tool tip. This can damages the tools and slow the milling process.

Figure 10A:
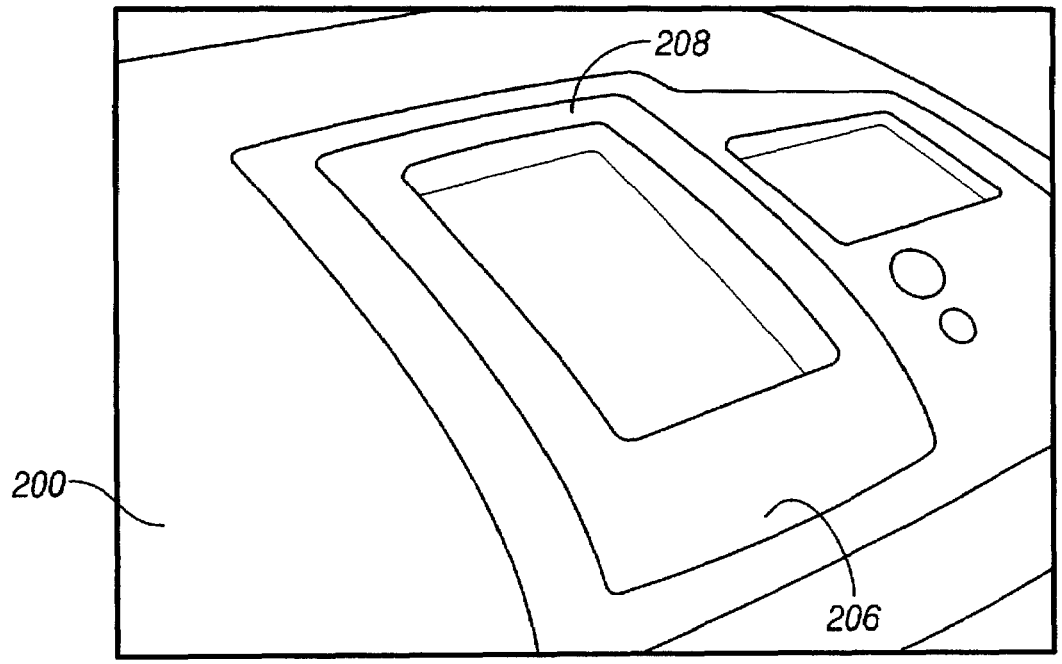
FIGS. 10a and 10b provide illustrations of the illuminated cover to the work area.
Figure 10B:
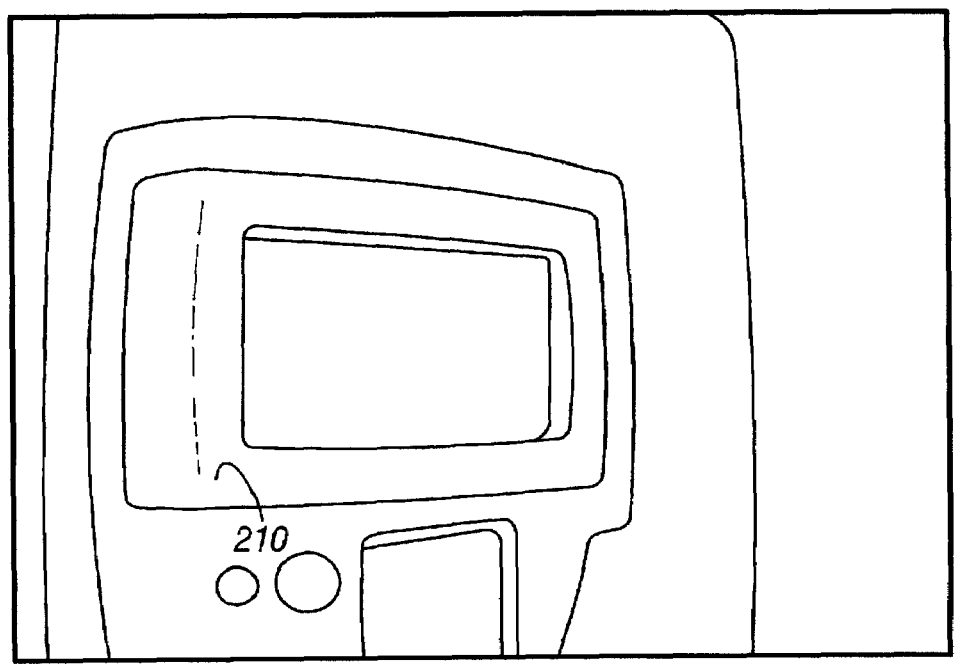

FIGS. 10a and 10b illustrate another innovation, namely the use of light to indicate the progress of a particular job. Alternate embodiment machine 200 is shown having a partially transparent cover 206 for the work area. The cover protects the technician from debris and the water stream that is cooling and cleaning the blank. If the technician walks away from the milling machine 200 to work on another project, the illumination of the cover may provide a means to communicate an error or other state of the machine to the technician at a distance. If an error occurs, lights 208 could illuminate providing the technician with an indication to return. In another scenario, lights 208 are illuminated whenever the machine is powered. The color of lights 208 changes depending on the condition of the job. White light might indicate that the machine is not in use. Green light might indicate that a current job is progressing smoothly. Red light might indicate an error has occurred. Thus, a simple glance by the technician tells him the status of the machine. Lights can be on one edge of the door 206 as shown in FIG. 10*a*, or on several edges as shown in FIG. 10*b*. The lights 208 may comprise LEDs, which may be illuminated at variable intensity levels. The lights 208 may comprise an array of equal numbers of Red, Green and Blue LEDs. An LED may be a multicolor type. The light from each of the LEDs travels within and is scattered within and without the partially transparent 206 by the process of internal reflection. Therefore, the light is scattered throughout the cover 206, even if the cover has surfaces which are curved, or sharp corners or features. The scattered light illuminates the mill chamber, and provides a powerful communication means to communicate the status of the milling machine to a user who may observe the milling machine at a distance. By utilizing an array of red, green and blue LEDs, each of which may be illuminated at any desired intensity level, any color combination is possible. The light from each of the LEDs is substantially mixed and combined within the partially transparent cover, so that any desired resultant color is possible. For example, by having the Red and Blue LEDs on at full intensity and the Green LEDs off, results in a bright magenta combined color. In the same way, a Cyan color may be produced by turning off the Red LEDs, and illuminating the Green and Blue LEDs at full intensity. In this manner, operating states (e.g., each of a different color) may be indicated.

Error can be detected in several ways. One is simply a feedback on the speed of the tools, or the power load on the spindle motors. If the speed drops under a predetermined minimum, or the power load changes abruptly indicating a broken tool, then the lights 30 can signal red. Another feedback is based on the position of the tool tips. A control system can track the outer contours of the milled blank. If that outer surface deviates from the planned outer surface, then an error has occurred.

Figure 11A:
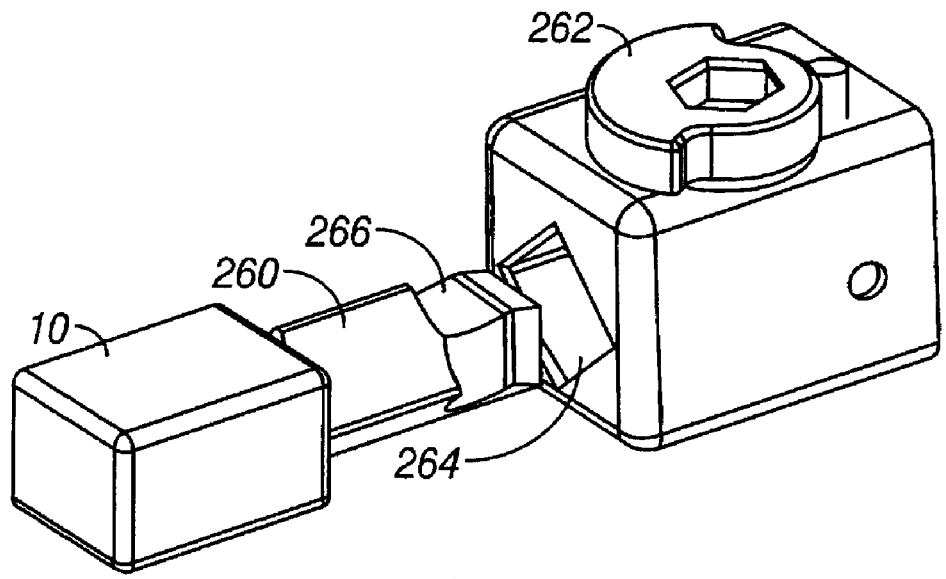
FIGS. 11a and 11b illustrate an alternative embodiment for the mandrel used to secure the work piece.
Figure 11B:
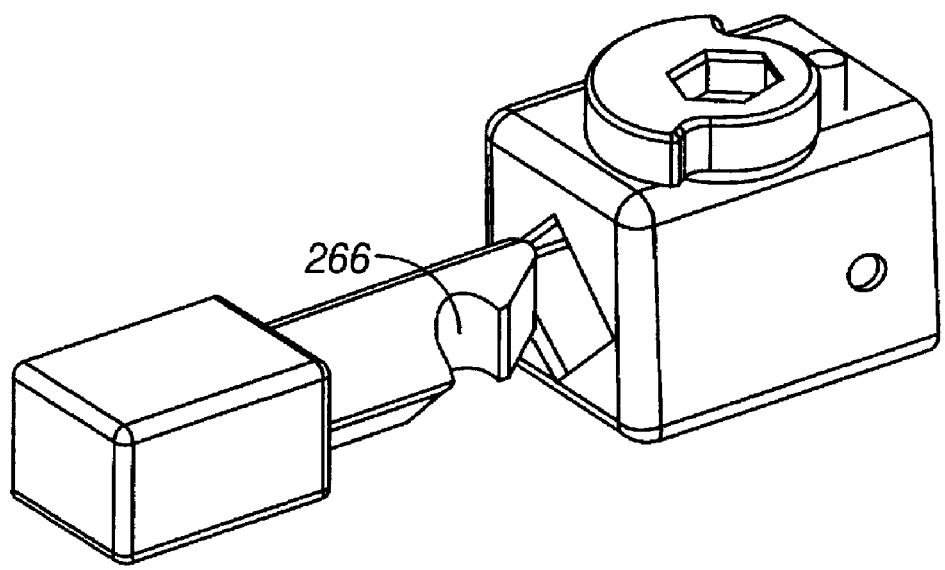

Another source of error is poor positioning of the blank. The blank is coupled to the milling machine with a mandrel that engages a mandrel socket. FIGS. 11*a* and 11*b* show a mandrel with blank engaging a mandrel socket in more detail. The mandrel 260 has a distal end that enters a similarly shaped socket 264. As shown the mandrel has a generally square cross-section that engages a similarly shaped socket. A groove 266 near the distal end of the socket provides an engagement surface for a cam 262. The cam 262 is rotated to a first position to allow insertion of the mandrel 260. The cam 262 is then rotated to a second position that engages the groove and secures the mandrel within the socket.

Figure 12A:
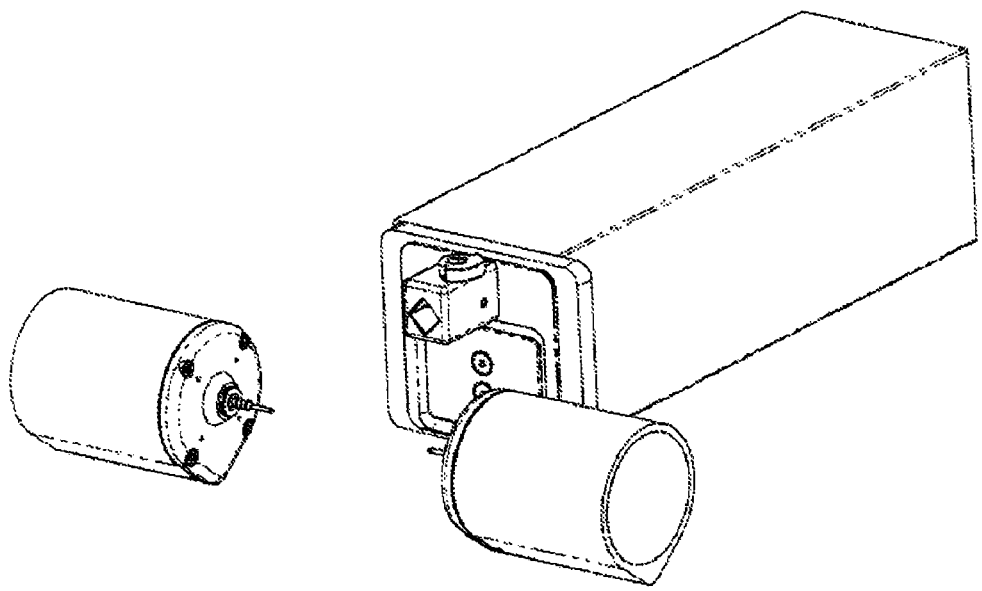
FIGS. 12a and 12b illustrate how the tool changer of the milling machine is positionable within the motion system envelope according to the present invention.
Figure 12B:
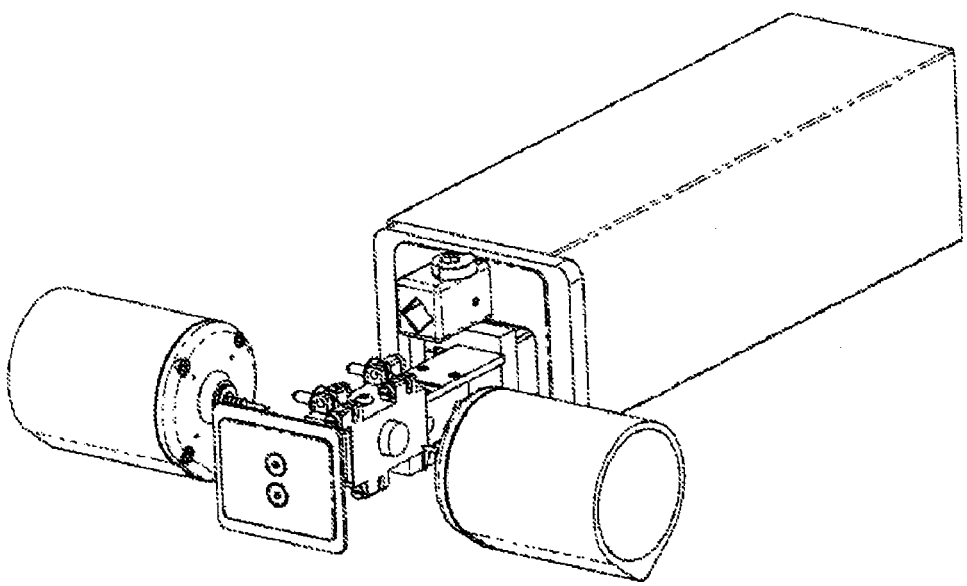

FIGS. 12*a* and 12*b* show another illustration of the tool changer and how it is carried within the blank holder assembly. This layout (which is described and illustrated above) is quite useful as the general motion system used for milling also is used to perform a tool change, without having to extend the motion limits (i.e. the tool changer places the tools into the same envelope of motion used for milling). In conventional approaches, the tool changer is positioned off to one side or the other relative to the milling area; this dictates that the mill motion system have a much larger range of motion just to be able to retrieve a tool. This is undesirable, and it typically increases the size of the mill. According to the present invention, as previously described and illustrated, the tool changer is located in the subassembly 140 (see FIG. 4) and, in particular, within carriage 142 therein that is movable from a closed position (FIG. 12*a*) to an open position (FIG. 12*b*). As has been described above, the subassembly 140 moves a blank along a first (e.g., Y) axis and a second (e.g., Z) axis, where the second axis is orthogonal to the first axis and the first and second axes define a plane. The pair of spindles (see FIG. 2, FIG. 5 or FIG. 9) in effect are located on opposite sides of the plane, and each spindle moves in an third (e.g., X) axis, which is orthogonal to the first and second axes. As seen in FIG. 5, for example, a tool is retrieved to a spindle by moving the tool changer through the first and second axes while simultaneously positioning the spindle along the third axis. In like manner, either spindle may retrieve a tool.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. In a milling machine having an assembly, a pair of opposed spindles, and a tool changer movable along first and second axes and carried within the assembly, wherein the assembly also supports a blank to be milled by the pair of opposed spindles, the opposed spindles both movable along a third axis and the opposed spindles accepting tools such that the tools face one another in opposite directions along the third axis, a tool change method comprising:
   retrieving a tool from the tool changer to one of the spindles by moving the tool changer through the first and second axes while simultaneously positioning the one spindle along the third axis;
   wherein a tool change is carried out within a same envelope of motion used for milling the blank.

2. The method as described in claim 1 wherein the second axis is orthogonal to the first axis, the first and second axes define a plane, and the third axis is orthogonal to the first and second axes.

3. The method as described in claim 2 wherein the assembly moves along the first axis and the second axis.

4. The method as described in claim 1 wherein retrieving the tool from the tool changer comprises selecting the tool from a plurality of tools within the tool changer.

5. The method as described in claim 4 wherein the tool is selected from the plurality of tools based on a material of the blank to be milled.

6. The method as described in claim 4 further comprising utilizing a camera to inspect a tip of the tool.

7. The method as described in claim 6 further comprising retrieving a backup tool from the plurality of tools.

8. The method as described in claim 1 wherein each of the opposed spindles is coupled to a frame movably mounted to a pair of rails extending parallel to the third axis, and wherein positioning the one spindle along the third axis includes moving the frame of the one spindle along the pair of rails to a desired position.

9. In a milling machine having an assembly, a first spindle coupled to a first frame, a second spindle coupled to a second frame, and a tool changer carried within the assembly and movable along first and second axes, wherein the assembly supports a blank to be milled by the first and second spindles, wherein the first and second frames are each movable along a third axis, and wherein the first and second spindles are oriented opposite one another and configured to accept a tool such that the tools face one another in opposite directions of the third axis, a tool change method comprising:
   retrieving a first tool from the tool changer to the first spindle by moving the tool changer through the first and second axes while simultaneously positioning the first frame along the third axis;
   wherein a tool change is carried out within a same envelope of motion used for milling the blank.

10. The method as described in claim 9 wherein the second axis is orthogonal to the first axis, the first and second axes define a plane, and the third axis is orthogonal to the first and second axes.

11. The method as described in claim 10 wherein the assembly moves along the first axis and the second axis.

12. The method as described in claim 9 wherein retrieving the first tool from the tool changer comprises selecting the first tool from a plurality of tools within the tool changer.

13. The method as described in claim 12 wherein the first tool is selected from the plurality of tools based on a material of the blank to be milled.

14. The method as described in claim 12 further comprising inspecting a tip of the first tool.

15. The method as described in claim 14 further comprising retrieving a backup tool from the plurality of tools.

16. The method as described in claim 9 wherein the first spindle and the second spindle are aligned.

17. The method as described in claim 9 wherein the first spindle and the second spindle are offset.

18. The method as described in claim 17 wherein the first spindle and the second spindle are offset by a distance equal to or greater than a diameter of the first tool.

19. The method as described in claim 9 further comprising retrieving a second tool from the tool changer to the second spindle by moving the tool changer through the first and second axes while simultaneously positioning the second frame along the third axis.

20. The method as described in claim 19 wherein retrieving the second tool from the tool changer comprises selecting the second tool from a plurality of tools within the tool changer.

* * * * *